(12) United States Patent
Seto et al.

(10) Patent No.: US 7,306,660 B2
(45) Date of Patent: Dec. 11, 2007

(54) ODOR ELIMINATING MATERIAL AND MANUFACTURING METHOD THEREOF

(75) Inventors: Yasutaro Seto, Osaka (JP); Tatsuo Nakamura, Nara (JP); Yoshiharu Nishino, Nara (JP); Shuichi Yonezawa, Wakayama (JP); Shuichi Gennaka, Nara (JP)

(73) Assignee: Suminoe Textile Co., Ltd., Osakashi (JP)

( * ) Notice: Subject to any disclaimer, the term of this patent is extended or adjusted under 35 U.S.C. 154(b) by 996 days.

(21) Appl. No.: 10/658,556

(22) Filed: Sep. 10, 2003

(65) Prior Publication Data

US 2004/0219126 A1 Nov. 4, 2004

(30) Foreign Application Priority Data

Apr. 30, 2003 (JP) .............................. 2003-125046

(51) Int. Cl.
*A61L 9/00* (2006.01)
*B01D 20/32* (2006.01)

(52) U.S. Cl. .................. 96/154; 55/524; 424/76.1; 424/76.8; 422/120; 540/139

(58) Field of Classification Search .................. 96/108, 96/153, 154; 95/285; 55/524; 424/76.1, 424/76.8; 422/120, 122; 540/122, 139
See application file for complete search history.

(56) References Cited

U.S. PATENT DOCUMENTS 5,047,022 A * 9/1991 Hasebe et al. ............... 604/359
5,883,245 A * 3/1999 Yamasaki et al. ........... 540/140
6,335,075 B1 * 1/2002 Seto et al. .................... 428/96
6,521,553 B1 * 2/2003 Tabata et al. ............... 442/123

FOREIGN PATENT DOCUMENTS

| JP | 05269328 A | 10/1993 |
|----|------------|---------|
| JP | 11-137653 | 5/1999 |
| JP | 02-180634 | 7/1999 |
| JP | 2000084057 A | 3/2000 |
| JP | 2000-152979 | 6/2000 |
| JP | 2000152982 A | 6/2000 |
| JP | 2000328438 A | 11/2000 |
| JP | 2001-009019 | 1/2001 |
| JP | 2001254269 A | 9/2001 |

OTHER PUBLICATIONS

Japanese Office Action dated Oct. 18, 2005 w/English translation.

* cited by examiner

*Primary Examiner*—Frank M. Lawrence
(74) *Attorney, Agent, or Firm*—Edwards Angell Palmer & Dodge LLP

(57) ABSTRACT

A cationized supporting material 2 is immersed into a treatment solution containing a level dyeing agent, and then immersed into a treatment solution containing a metal phthalocyanine complex and then dried to thereby obtain an odor eliminating material 1. Alternatively, a cationized supporting material 2 is immersed into a treatment solution containing a metal phthalocyanine complex and a migration inhibitor and then dried to thereby obtain an odor eliminating material 1. The odor eliminating material exerts excellent odor elimination performance against ammonia, hydrogen sulfide, methyl mercaptan, acetic acid and acetaldehyde.

33 Claims, 1 Drawing Sheet

ODOR ELIMINATING MATERIAL AND MANUFACTURING METHOD THEREOF

Priority is claimed to Japanese Patent Application No. 2003-125046, filed on Apr. 30, 2003, the disclosure of which is incorporated by reference in its entirety.

BACKGROUND OF THE INVENTION

1. Field of the Invention

The present invention relates to an odor eliminating material that can be used, for example, as an odor eliminating sheet, an odor eliminating filter for air-conditioners or the like, and also relates to the manufacturing method thereof.

2. Description of Related Art

The following description sets forth the inventor's knowledge of related art and problems therein and should not be construed as an admission of knowledge in the prior art.

In accordance with the recent improvement of life environments, a strong interest is directed to elimination of living odors in living spaces, such as odors of ammonia, trimethylamine, hydrogen sulfide, methyl mercaptan, acetic acid, acetaldehyde or the like, to secure a more comfortable living space.

In order to solve odor problems, various kinds of odor eliminating materials are available in markets. For example, an odor eliminating material in which activated carbon is carried on a surface of a nonwoven fabric is known. Although this kind of adsorption type odor eliminating material is excellent in immediate effect, there are defects such that it is poor in continuous effect and extremely short in life.

In recent years, as an odor eliminating material, an odor eliminating sheet in which metal phthalocyanine complexes are carried by a cloth (see Japanese Unexamined Patent Publication No. 2000-84057 A) and an odor eliminating paper in which metal phthalocyanine complexes are carried by a thin paper (see Japanese Unexamined Patent Publication No. 05-269328 A) have been proposed. However, these odor eliminating sheets/papers were not enough in odor elimination performance. Also known is an odor eliminating material in which metal phthalocyanine complexes are adhered by binder resin (see Japanese Unexamined Patent Publication No. 2000-152982 A). However, enough odor elimination performance could not be obtained by this odor eliminating material. Under the circumstances, a textile product in which metal phthalocyanine complexes are carried by cationized cellulose series fibers has been proposed (see Japanese Unexamined Patent Publication No. 2001-254269 A).

On the other hand, an odor eliminating material in which photocatalyst such as titanium oxide is carried by a cloth has also been proposed (see Japanese Unexamined Patent Publication No. 2000-328438 A).

However, the aforementioned conventional prior art techniques had the following drawbacks. That is, in the textile products disclosed in Japanese Unexamined Patent Publication No. 2001-254269 A, although odor eliminating effects can be improved by cationizing cellulose series fibers in advance to increase the carried amount of the metal phthalocyanine complex to some degree, the odor elimination performance was not fully satisfactory. Therefore, it is desired to further improve the odor elimination performance. A further increased concentration of the metal phthalocyanine complex at the time of the immersion treatment would not cause a further increased carried amount. Therefore, it was difficult to further improve the odor elimination performance.

In the aforementioned odor eliminating material carrying photocatalyst, although there is a feature that various kinds of odor components can be decomposed at normal temperature, it is required to irradiate ultraviolet rays of certain wavelengths to photocatalyst in order to exert the decomposition, which limits the application environment as odor eliminating materials. Furthermore, the odor elimination performance was not enough.

The description herein of advantages and disadvantages of various features, embodiments, methods, and apparatus disclosed in other publications is in no way intended to limit the present invention. Indeed, certain features of the invention may be capable of overcoming certain disadvantages, while still retaining some or all of the features, embodiments, methods, and apparatus disclosed therein.

SUMMARY OF THE INVENTION

It is an object of the present invention to provide an odor eliminating material excellent in odor elimination performance against ammonia, hydrogen sulfide, methyl mercaptan, acetic acid, acetaldehyde or the like and long in life. It is another object of the present invention to provide a method for manufacturing such an odor eliminating material.

According to an odor eliminating material of the present invention, the odor eliminating material comprises:
a cationized supporting material; and
a metal phthalocyanine complex carried by the supporting material,
wherein the supporting material is treated by a treatment agent containing a metal phthalocyanine complex and a level dyeing agent, or treated by a treatment agent containing a level dyeing agent and then further treated by a treatment agent containing a metal phthalocyanine complex, whereby the metal phthalocyanine complex is carried by the supporting material.

According to an odor eliminating material according to another aspect of the present invention, an odor eliminating material comprises:
a cationized supporting material;
a metal phthalocyanine complex carried by the supporting material; and
a level dyeing agent carried by the supporting material.

In either odor eliminating material, since the supporting material is cationized, the carried amount of the metal phthalocyanine complex increases. In addition, since the treatment by the level dyeing agent is also performed, the carried amount of the metal phthalocyanine complex increases remarkably. As a result, an odor of ammonia, hydrogen sulfide, methyl mercaptan, acetic acid, acetaldehyde or the like can be eliminated fully. Furthermore, a long-acting odor elimination performance can be obtained.

It is preferable that the level dyeing agent is one or more compounds selected from the group consisting of polyalkylether sulfonic acid, polyoxyethylene alkylether, alkyl succinic acid and alkyl sulfonic acid. This further increases the carried amount of the metal phthalocyanine complex, which further improves the odor eliminating performance.

According to another odor eliminating material of the present invention, the odor eliminating material comprises:
a cationized supporting material; and
a metal phthalocyanine complex carried by the supporting material, wherein the supporting material is treated by a treatment agent containing a metal phthalocyanine complex and a migration inhibitor, or treated by a treatment agent containing a migration inhibitor and then further treated by a treatment agent containing a metal phthalocyanine complex, whereby the metal phthalocyanine complex is carried by the supporting material.

Furthermore, according to still another odor eliminating material of the present invention, the odor eliminating material, comprises:

a cationized supporting material;

a metal phthalocyanine complex carried by the supporting material; and a migration inhibitor carried by the supporting material.

In either odor eliminating material, since the supporting material is cationized, the carried amount of the metal phthalocyanine complex increases. In addition, since the treatment by the migration inhibitor is also performed, the carried amount of the metal phthalocyanine complex increases remarkably. As a result, an odor of ammonia, hydrogen sulfide, methyl mercaptan, acetic acid, acetaldehyde or the like can be eliminated fully. Furthermore, a long-acting odor elimination performance can be obtained.

It is preferable that the migration inhibitor is one or more compounds selected from the group consisting of acrylamide series polymer and sodium alginate. In this case, the carried amount of the metal phthalocyanine complex further increases, resulting in an improved odor elimination performance.

In either odor eliminating material according to the present invention, it is preferable that a constituent material of the supporting material is one or more materials selected from the group consisting of cellulose, rayon, cotton and wool. In these materials, since they have a number of hydroxyl functions as reactive sites for cationization, the cationization amount increases, which in turn further increases the carried amount of metal phthalocyanine complex.

It is preferable that the supporting material is constituted by a sheet made of any one of nonwoven fabric, woven fabric, knitted fabric and paper (the supporting material may be a sheet-like member or maybe formed into a three-dimensional member formed by combining these sheet-like members). In cases where the supporting material is constituted as mentioned above, the surface area in contact with air increases remarkably, resulting in an improved odor eliminating efficiency, which enables quick odor elimination.

It is preferable that the supporting material is a material cationized by quaternary ammonium salt. In this case, the carried amount of the metal phthalocyanine complex further increases, which further improves the odor elimination performance.

It is preferable that the metal phthalocyanine complex is a cobalt phthalocyanine complex. In this case, the odor elimination performance for methyl mercaptan and acetic acid can be further improved.

Furthermore, in cases where the supporting material further carries a hydrazine derivative, a further improved odor elimination performance can be obtained.

A method for manufacturing an odor eliminating material, comprises:

cationizing a supporting material;

immersing the cationized supporting material into a treatment solution containing a level dyeing agent; and immersing the supporting material treated in the treatment solution into a treatment solution containing a metal phthalocyanine complex and then drying the supporting material.

In this method, since the cationized supporting material is immersed into a treatment solution containing a level dyeing agent in advance and then immersed into the treatment solution containing a metal phthalocyanine complex, a larger amount of metal phthalocyanine complex can be carried by the supporting material. As a result, an odor of ammonia, hydrogen sulfide, methyl mercaptan, acetic acid, acetaldehyde or the like can be eliminated fully. Furthermore, the odor eliminating material has an enough long-term odor elimination performance. Further, since the supporting material is immersed into the treatment solution, the metal phthalocyanine complex can be evenly carried by the supporting material.

According to another method for manufacturing an odor eliminating material of the present invention, the method comprises:

cationizing a supporting material; and immersing the cationized supporting material into a treatment solution containing a metal phthalocyanine complex and a migration inhibitor and then drying the supporting material.

In this method, since the cationized supporting material is immersed into the treatment solution containing both of the metal phthalocyanine complex and the migration inhibitor, a larger amount of the metal phthalocyanine complex can be carried by the supporting material. As a result, the obtained odor eliminating material can fully eliminate an odor of ammonia, hydrogen sulfide, methyl mercaptan, acetic acid, acetaldehyde or the like. Furthermore, this odor eliminating material has an enough long-term odor elimination performance. Further, since the supporting material is immersed into the treatment solution, the metal phthalocyanine complex can be evenly carried by the supporting material.

In the latter manufacturing method, it is preferable that a mass ratio of the metal phthalocyanine complex/the migration inhibitor in the treatment solution falls within a range of 1/10 to 10/1. In this case, the carried amount of the metal phthalocyanine complex can be further increased, which in turn can further improve the odor elimination performance.

Furthermore, according to still another odor eliminating material of the preset invention, an odor eliminating material, comprises:

a supporting material; and an odor eliminating compound carried by the supporting material, wherein the supporting material is treated by a treatment agent containing the odor eliminating compound including a hydrazine derivative and a metal phthalocyanine complex, whereby the odor eliminating compound is carried by the supporting material. With this odor eliminating material, an odor of ammonia, hydrogen sulfide, methyl mercaptan, acetic acid, acetaldehyde or the like can be eliminated fully because of the synergistic effects of the carried hydrazine derivative and metal phthalocyanine complex. Furthermore, the odor eliminating material has an enough long-term odor elimination performance.

It is preferable that a weight ratio of the hydrazine derivative and the metal phthalocyanine complex in the treatment solution falls within a range of 75/25 to 95/5. This specific ratio causes outstanding synergistic effects of the hydrazine derivative and the metal phthalocyanine complex, which remarkably improves the odor elimination performance.

It is preferable that the odor eliminating compound further contains a porous inorganic substance. The porous inorganic substance is excellent in odor component capturing function, and therefore the odor component, which was effectively captured by the porous inorganic substance, can be fully eliminated by the decomposing functions of the hydrazine derivative and the metal phthalocyanine complex. These cooperated functions improve the odor elimination performance.

It is preferable to use zeolite as the porous inorganic substance. In this case, since zeolite is excellent in odor capturing performance, the odor elimination performance can be further improved.

It is preferable that the odor eliminating compound further contains binder resin. In this case, since other components (e.g., the hydrazine derivative, the metal phthalocyanine complex, the porous inorganic substance) in the odor eliminating composition can be assuredly carried by the binder resin, it is effectively prevented that each component of the odor eliminating composition is detached from the supporting material, which in turn further improves the sustainability of the odor eliminating performance.

It is preferable to use cobalt phthalocyanine complex as the metal phthalocyanine complex. In this case, the odor elimination performance especially for methyl mercaptan and acetic acid can be further improved.

From the view point of sufficiently securing odor elimination performance without increasing costs, it is preferable that the carried amount of the odor eliminating compound falls within a range of 0.1 to 10 wt % with respect to the supporting material.

In cases where a nonwoven fabric is used as the supporting material, the odor eliminating material can be used, for example, as building materials. Furthermore, since the odor eliminating material can be formed into a sheet-like item, no large installation space will be required and it can be deformed flexibly. As a result, it can be applied to various usage and excellent in versatility.

In cases where porous structure material is used as the supporting material, the contact surface area per unit area increases, the odor eliminating material can be preferably used, for example, as an odor eliminating filter for air-conditioning systems such as air conditioners or an odor eliminating filter for various odor eliminating apparatuses.

It is preferable that the hydrazine derivative is a reaction product of one or two compounds selected from the group consisting of hydrazine and semicarbazide and one or more compounds selected from the group consisting of monocarboxylic acid having the carbon number of 8 to 16, dicarboxylic acid, aromatic monocarboxylic acid and aromatic dicarboxylic acid. In this case, the odor eliminating material can be excellent in odor elimination performance.

It is also preferable that the hydrazine derivative is a reaction product of one or two compounds selected from the group consisting of hydrazine and semicarbazide and one or more compounds selected from the group consisting of monoglycidyl derivative and diglycidyl derivative having the carbon number of 8 to 16. In this case, the odor eliminating material can be excellent in odor elimination performance.

In cases where the hydrazine derivative is one or more compounds selected from the group consisting of sebacic acid dihydrazide, dodecanedioic dihydrazide and isophthalic acid dihydrazide, a further improved odor eliminating performance can be obtained.

According to a method for manufacturing an odor eliminating material, the method comprises:

immersing a supporting material into a treatment agent containing an odor eliminating composite including a hydrazine derivative and a metal phthalocyanine complex; and drying the supporting material to thereby carry the odor eliminating composite.

The odor eliminating material manufactured by the method can effectively eliminate an odor of ammonia, hydrogen sulfide, methyl mercaptan, acetic acid, acetaldehyde or the like because of the synergistic effects of the carried hydrazine derivative and metal phthalocyanine complex. Furthermore, the durability of the odor elimination performance can be extended. In addition, since the supporting member is immersed in the treatment solution, the odor eliminating composition can be carried evenly by the supporting member.

According to another method for manufacturing an odor eliminating material, the method comprises:

coating a treatment agent containing an odor eliminating composite including a hydrazine derivative and a metal phthalocyanine complex on a sheet-like supporting material; and drying the supporting material to thereby carry the odor eliminating composite.

The odor eliminating material manufactured by the method can effectively eliminate an odor of ammonia, hydrogen sulfide, methyl mercaptan, acetic acid, acetaldehyde or the like because of the synergistic effects of the carried hydrazine derivative and metal phthalocyanine complex. Furthermore, the durability of the odor elimination performance can be extended. In addition, since a coating method is employed, the productivity can be remarkably improved and the controlling of the carried amount can be performed at high precision.

Other objects and the features will be apparent from the following detailed description of the present invention with reference to the attached drawings.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/ or advantages of particular embodiments should not be construed as limiting other embodiments or the claims.

BRIEF DESCRIPTION OF THE DRAWINGS

The accompanying figures are provided by way of example, without limiting the broad scope of the invention or various other embodiments, wherein.

DETAILED DESCRIPTION OF THE PREFERRED EMBODIMENTS

According to a first aspect of the present invention, an odor eliminating material 1 includes a cationized supporting material 2 and a metal phthalocyanine complex carried by the supporting material. The supporting material 2 is treated by a treatment agent containing a metal phthalocyanine complex and a level dyeing agent, or treated by a treatment agent containing a level dyeing agent and then further treated by a treatment agent containing a metal phthalocyanine complex, whereby the metal phthalocyanine complex is carried by the supporting material 2. In this odor eliminating material, since the supporting material 2 is cationized in advance, the carried amount of the metal phthalocyanine complex increases. In addition, since the treatment by the level dyeing agent is also performed, the carried amount of the metal phthalocyanine complex increases remarkably. As a result, an odor of ammonia, hydrogen sulfide, methyl mercaptan, acetic acid, acetaldehyde or the like can be eliminated fully. Although an immersion method and a coating method can be exemplified as the aforementioned treating method, any other method can also be employed. Furthermore, in the odor eliminating material 1 according to the first aspect of the present invention, the level dyeing agent used for the treatment can be carried by the odor eliminating material, or can be removed from the odor eliminating material by cleaning or the like.

According to the second aspect of the present invention, the odor eliminating material 1 includes:

a cationized supporting material 2; and a metal phthalocyanine complex carried by the supporting material, wherein the supporting material 2 is treated by a treatment agent containing a metal phthalocyanine complex and a migration inhibitor, or treated by a treatment agent containing a migration inhibitor and then further treated by a treatment agent containing a metal phthalocyanine complex, whereby the metal phthalocyanine complex is carried by the supporting material 2. In this odor eliminating material 1, since the supporting material 2 is cationized in advance, the carried amount of the metal phthalocyanine complex increases. In addition, since the treatment by the migration inhibitor is also performed, the carried amount of the metal phthalocyanine complex increases remarkably. As a result, an odor of ammonia, hydrogen sulfide, methyl mercaptan, acetic acid, acetaldehyde or the like can be eliminated fully. Although an immersion method and a coating method can be exemplified as the aforementioned treating method, any other method can also be employed. Furthermore, in the odor eliminating material 1 according to the second aspect of the present invention, the migration inhibitor used for the treatment can be carried by the odor eliminating material. However, it is preferable that the migration inhibitor is removed from the odor eliminating material 1 by cleaning or the like.

Figure 1:
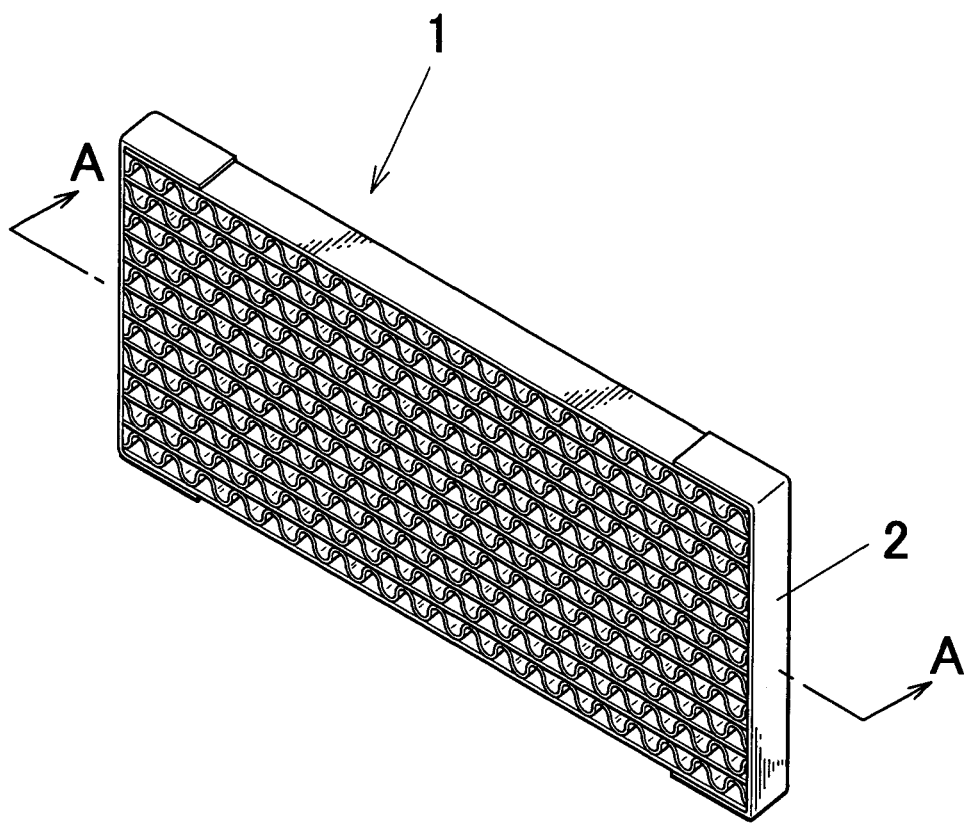
FIG. 1 is a perspective view showing an odor eliminating material according to one embodiment of the present invention.
Figure 2:
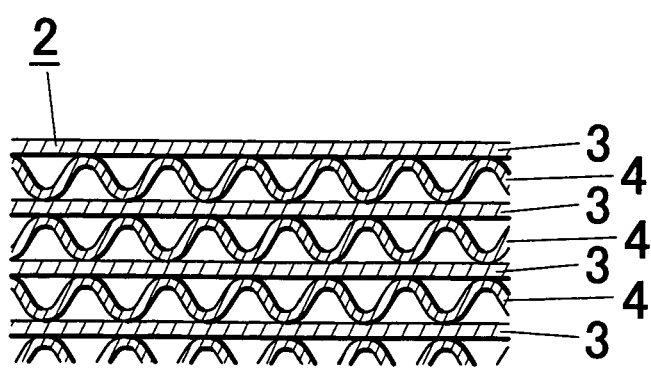
FIG. 2 is an enlarged cross-sectional view taken along the line A-A in FIG. 1.

As the supporting material 2, any material can be used provided that it can carry the metal phthalocyanine complex. For example, a nonwoven fabric sheet, a woven fabric sheet, a knitted fabric sheet, a paper sheet and a porous three-dimensional structure can be exemplified. As the nonwoven fabric sheet, for example, a spunbonded nonwoven fabric, a needle-punched nonwoven fabric, a chemical bonded nonwoven fabric, a nonwoven fabric manufactured by a melt blow method can be exemplified. As the porous three-dimensional structure, for example, a honeycomb structure and a porous three-dimensional structure in which flat sheets 3 and wavy sheets 4 are alternatively laminated and integrally secured as shown in FIGS. 1 and 2 can be exemplified.

Although the structural material of the supporting material 2 is not specifically limited, it is preferable to use a material having a number of hydroxyl functions (OH functions) as cationization reactive points. As such a material, cellulose (e.g., pulp), rayon, cotton and wool can be exemplified. The mixture of these materials can also be used.

The metal phthalocyanine complex is not limited to a specific one. For example, an iron phthalocyanine complex and a cobalt phthalocyanine complex can be exemplified. Especially, it is preferable to use a cobalt phthalocyanine complex. In this case, the performance for eliminating an odor of methyl mercaptan and acetic acid can be further improved. Although the cobalt phthalocyanine complex is not limited to a specific one, for example, cobalt phthalocyanine polysulfonic acid natrium, cobalt phthalocyanine octacarboxylic acid and cobalt phthalocyanine tetracarboxylic acid can be exemplified.

Although the cationization treatment can be any treatment provided that the treatment enables an introduction of a cation function into the chemical structure of the supporting material 2. It is more preferable that the cationization treatment is performed by quaternary ammonium salt. In this case, the carried amount of the metal phthalocyanine complex can be further increased. As the quaternary ammonium salt, 3-chloro-2-hydroxypropyl trimethylammoniumchloride, glycidyltrimethyl ammoniumchloride and condensation polymer of 3-chloro-2-hydroxypropyl trimethylammoniumchloride (see the following chemical formula) can be exemplified.

[FORMULA 1]

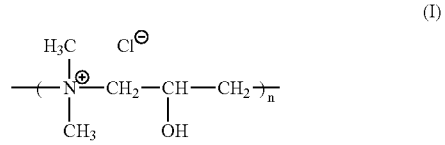

(I)

The cationization treatment will be explained while taking a cellulose fiber as an example. For example, it is presumed that 3-chloro-2-hydroxypropyl trimethylammoniumchloride reacts with hydroxyl function (mainly of the 6th grade primary hydroxyl function) of cellulose fiber under the existence of alkali as follows.

[Formula 2]

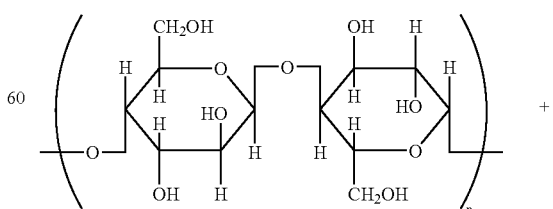

CELLULOSE FIBER

-continued

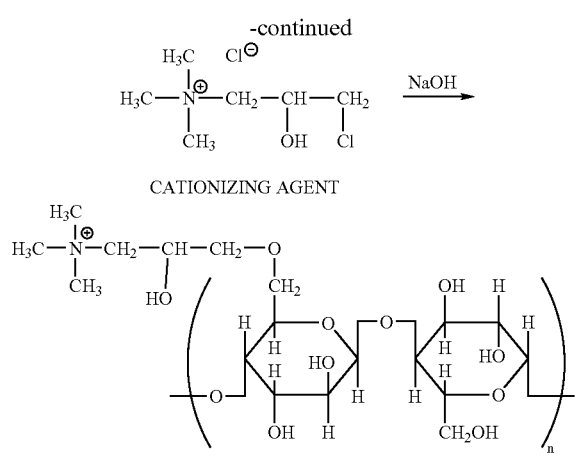

CATIONIZING AGENT

The level dyeing agent is a compound having a function for evenly dyeing an object with dyestuff and can be any compound having such a function. Among other things, it is preferable to use one or more compounds selected from the group consisting of polyalkylethel sulfonic acid, polyoxyethylene alkylethel, alkylsuccinic acid and alkylsulfonic acid. In this case, the carried amount of metal phthalocyanine complex can be further increased. It is more preferable to use one or more compounds selected from the group consisting of alkylsuccinic acid and alkylsulfonic acid. The aforementioned wordings of "polyalkylethel sulfonic acid," "alkylsuccinic acid" and "alkylsulfonic acid" are used to include the respective salt (i.e., polyalkylethel sulfonic acid salt, alkylsuccinic acid salt and alkylsulfonic acid salt).

The migration inhibitor is a compound having a function of preventing the movement of dyestuffs from a well-dyed portion of a fiber toward a slightly dyed portion thereof. Any compounds having such a function can be used as the migration inhibitor. Among other things, it is preferable to use one or more compounds selected from the group consisting of acrylamide series polymer and sodium alginate. In this case, the carried amount of metal phthalocyanine complex can be further increased. The most preferable one is acrylamide series polymer. As the acrylamide series polymer, polyacrylamide or acrylamide series copolymer in which acrylamide is copolymerized by one or more other monomer components.

In the odor eliminating members according to the first and second aspect of the present invention, another odor eliminating agent, odor capturing agent and/or additives can be carried by the supporting material 2. As the another odor eliminating agent, hydrazine derivative can be exemplified. As the odor capturing agent, porous inorganic substances such as activated carbon or zeolite can be exemplified.

As the hydrazine derivative, a reactant obtained by the reaction of hydrazine series compound and long-chain aliphatic compound or a reactant obtained by the reaction of hydrazine series compound and aromatic compound can be exemplified. The most preferable ones are a reaction product of one or more compounds selected from the group consisting of hydrazine and semicarbazide and one or more compounds selected from the group consisting of monocarboxylic acid having the carbon number of 8 to 16, dicarboxylic acid, aromatic monocarboxylic acid and aromatic dicarboxylic acid, or a reaction product of one or more compounds selected from the group consisting of hydrazine and semicarbazide and one or more compounds selected from the group consisting of monoglycidyl derivative and diglycidyl derivative whose carbon number is 8 to 16. By using the aforementioned hydrazine derivative, the odor eliminating performance can be further enhanced. As the reaction product, sebacic acid dihydrazide, dodecanedioic dihydrazide and isophthalic acid dihydrazide can be exemplified concretely. However, the reaction product is not limited to one of them.

In the odor eliminating materials 1 according to the first and second aspect of the present invention, the carried amount of the metal phthalocyanine complex can be increased remarkably by the functions of the level dyeing agent and the migration inhibitor. It is preferable to set the amount of the metal phthalocyanine complex to be 3,000 ppm or more with respect to the supporting material 2. In cases where the carried amount is set to fall within the range, a further improved odor elimination performance can be assuredly secured. The most preferable amount range is 5,000 ppm or more.

The odor eliminating material 1 according to the first aspect of the present invention can be manufactured, for example, as follows. First, the supporting member is subjected to a cationization treatment. The cationization treatment can be performed, for example, by immersing the supporting member into a treatment solution containing a cationizing agent. The treatment is preferably performed by setting the concentration of the cationizing agent so as to fall within the range of 0.5 to 10 mass %.

Next, the cationized supporting material is immersed in a treatment solution containing level dyeing agent. It is preferable that the concentration of the level dyeing agent is set so as to fall within the range of 0.2 to 5 mass %.

Subsequently, the supporting material taken out of the treatment solution is immersed in a treatment solution containing metal phthalocyanine complex, and then dried. It is preferable that the concentration of the metal phthalocyanine complex is set so as to fall within the range of 0.1 to 2 mass %.

In this manufacturing method, the cationized supporting material is immersed in the treatment solution containing the level dyeing agent in advance, and then immersed in the treatment solution containing the metal phthalocyanine complex. Therefore, a larger amount of metal phthalocyanine complex can be carried by the supporting material as compared with a method for immersing the supporting material in a treatment solution containing both the containing the level dyeing agent and the metal phthalocyanine complex.

The odor eliminating material 1 according to the second aspect of the present invention can be manufactured, for example, as follows. First, the supporting member is subjected to a cationization treatment. The cationization treatment can be performed, for example, by immersing the supporting member into a treatment solution containing a cationizing agent. The treatment is preferably performed by setting the concentration of the cationizing agent so as to fall within the range of 0.5 to 10 mass %.

Next, the cationized supporting material is immersed in a treatment solution containing the metal phthalocyanine complex and the migration inhibitor and then dried. At this time, it is preferable that the concentration of the metal phthalocyanine complex is set to be 0.1 to 2 mass % and the concentration of the migration inhibitor is set to be 0.05 to 5 mass %.

In this manufacturing method, the cationized supporting material is immersed in the treatment solution containing both the metal phthalocyanine complex and the migration inhibitor. Therefore, a larger amount of metal phthalocyanine complex can be carried by the supporting material as compared with a method (2 steps) in which the supporting material is first immersed in a treatment solution containing the migration inhibitor and then immersing in a treatment solution containing the metal phthalocyanine complex.

It is preferable that the mass ratio of the metal phthalocyanine complex/the migration inhibitor in the treatment solution falls within a range of 1/10 to 10/1. By setting the mass ratio so as to fall within the range, the carried amount of the metal phthalocyanine complex can be further increased. Among other things, it is preferable to set the mass ratio of the metal phthalocyanine complex/the migration inhibitor in the treatment solution so as to fall within a range of 1/2 to 5/1.

The odor eliminating material 1 according to the first and second aspects of the present invention is not necessarily limited to the above exemplified manufacturing method.

Although the application of the odor eliminating material 1 according to the first and second aspects of the present invention is not specifically limited, it can be used, for example, as odor eliminating sheets for building materials, odor eliminating filter for air-conditioning apparatuses such as air-conditioners or odor eliminating filters for various odor eliminating apparatuses.

Next, an odor eliminating material according to the third aspect of the present invention will be explained.

The odor eliminating material 1 according to the third aspect of the present invention includes a supporting material 2 and an odor eliminating compound carried by the supporting material, wherein the supporting material is treated by a treatment agent containing the odor eliminating compound including a hydrazine derivative and a metal phthalocyanine complex, whereby the odor eliminating compound is carried by the supporting material 2. According to this odor eliminating material, an odor of ammonia, hydrogen sulfide, methyl mercaptan, acetic acid, acetaldehyde or the like can be eliminated fully because of the synergistic effects of the carried hydrazine derivative and metal phthalocyanine complex.

As the supporting material 2, any material can be used provided that the material can carry the odor eliminating compositions. For example, a nonwoven fabric and a porous structure can be exemplified.

As for the nonwoven fabric sheet, the type is not limited to a specific one. For example, a spunbonded nonwoven fabric, a needle-punched nonwoven fabric, chemical bonded nonwoven fabric, a nonwoven fabric manufactured by a melt blow method can be exemplified. Furthermore, the materials of the fiber constituting these nonwoven fabrics are not limited to a specific one. For example, synthetic fibers such as polyester fibers, polyamide fibers or polypropylene fibers, regenerated fibers such as rayon fibers or natural fibers such as cotton or silk can be exemplified. Furthermore, the fibers constituting these nonwoven fabrics can be discontinuous fibers or continuous fibers. The length thereof and the thickness thereof are not specifically limited.

As the porous three-dimensional structure, for example, a honeycomb structure, a resin foam and a porous three-dimensional structure in which flat sheets 3 and wavy sheets 4 are alternatively laminated and integrally secured as shown in FIGS. 1 and 3 can be exemplified.

Next, the odor eliminating compositions of the odor eliminating material 1 according to the third aspect of the present invention will be explained. The odor eliminating compositions include a hydrazine derivative and a metal phthalocyanine complex as essential components. Needless to say, another odor eliminating agent, odor capturing agent and/or additives can be used together with the hydrazine derivative and the metal phthalocyanine complex.

As the hydrazine derivative, for example, a reactant obtained by the reaction of hydrazine series compound and long-chain aliphatic compound and a reactant obtained by the reaction of hydrazine series compound and aromatic compound can be exemplified.

Among other things, the most preferable ones are a reaction product of one or more compounds selected from the group consisting of hydrazine and semicarbazide and one or more compounds selected from the group consisting of monocarboxylic acid having the carbon number of 8 to 16, dicarboxylic acid, aromatic monocarboxylic acid and aromatic dicarboxylic acid, or a reaction product of one or more compounds selected from the group consisting of hydrazine and semicarbazide and one or more compounds selected from the group consisting of monoglycidyl derivative and diglycidyl derivative whose carbon number is 8 to 16. By using the aforementioned hydrazine derivative, the odor eliminating performance can be further enhanced. As the reaction product, sebacic acid dihydrazide, dodecane diacid dihydrazide and isophthalic acid dihydrazide can be exemplified concretely. However, the reaction product is not limited to one of them.

The metal phthalocyanine complex is not limited to a specific one. For example, an iron phthalocyanine complex, a cobalt phthalocyanine complex, nickel phthalocyanine complex and copper phthalocyanine complex can be exemplified. Especially, it is preferable to use a cobalt phthalocyanine complex. In this case, the performance for eliminating an odor of methyl mercaptan and acetic acid can be further improved.

It is preferable that the weight ratio of the hydrazine derivative and the metal phthalocyanine complex in the treatment solution falls within a range of 75/25 to 95/5. In this specific range, as will be apparent from the comparison data of the following examples, the synergistic effects of the hydrazine derivative and the metal phthalocyanine complex can be exerted remarkably, causing an improved odor eliminating performance. To the contrary, if the weight ratio does not fall within the range, the odor elimination performance decreases. Further, it is not preferable to use an excess metal phthalocyanine complex since an excess usage ratio of the metal phthalocyanine complex causes an increased cost.

In the third aspect of the present invention, it is preferable that the odor eliminating compound further contains a porous inorganic substance. The porous inorganic substance is excellent in odor component capturing functions, and therefore the odor component, which was effectively captured by the porous inorganic substance, can be fully eliminated by the decomposing functions of the hydrazine derivative and the metal phthalocyanine complex. These cooperated functions improve the odor elimination performance.

As the porous inorganic substance, although it is not limited to a specific one, for example, activated carbon and zeolite can be exemplified. Among other things, it is preferable to use zeolite as the porous inorganic substance. In this case, the odor capturing performance can be improved, and the quick odor elimination performance can be further improved.

Furthermore, it is preferable that the odor eliminating compound further contains binder resin. In this case, since other components (e.g., the hydrazine derivative, the metal phthalocyanine complex, the porous inorganic substance) in the odor eliminating composition can be assuredly carried by the supporting material with the binder resin, it is effectively prevented that each component of the odor eliminating composition is detached from the supporting material, which in turn further improves the sustainability of the odor eliminating performance.

As the binder resin, it is not limited to a specific one. The examples of the binder resin include acrylate resin, methacrylate resin, urethane resin, silicone resin, glyoxal resin, polyvinyl acetate, polyvinylidene chloride, butadiene resin, melamine resin, epoxy resin, acrylic-silicone copolymer resin, ethylene-vinyl acetate copolymer resin, isobutylene-maleic anhydride copolymer resin, ethylene-styrene-acrylate-methacrylate copolymer resin. Two or more aforementioned resins can be combined into the binder resin.

It is preferable that the carried amount of the odor eliminating compound falls within a range of 0.1 to 10 wt % with respect to the supporting material. If the carried amount is less than 0.1 wt %, enough odor eliminating effects cannot be obtained, and the immediate effect deteriorates. Therefore, it is not preferable. On the other hand, if the carried amount exceeds 10 wt %, the cost increases. Therefore, it is also not preferable.

The odor eliminating member 1 according to the third aspect of the present invention can be manufactured, for example, as follows. First, a treatment agent, which is water dispersion liquid in which various components of the odor eliminating compositions are dispersed, is prepared. At this time, it is preferable to disperse these odor eliminating compositions as evenly as possible. In cases of using binder resin, it is preferable to form emulsion between the binder resin and water. As the dispersion medium, although alcohol can be used other than water, water is preferably used. Various additives can be added to the aforementioned treatment agent for the purpose of improving the property of dispersing agent and/or thickening agent.

The supporting material is treated by using the treatment agent to thereby carry the odor eliminating compositions. There are two preferable methods. According to the first manufacturing method, the supporting material is immersed in the treatment agent and then dried to thereby carry the odor eliminating compositions on the supporting material. By employing this immersion method, the odor eliminating compositions can be carried by the supporting material, which enables a manufacturing of a high quality odor eliminating material.

According to the second manufacturing method, the treatment agent is coated on the sheet-shaped supporting material, and then the supporting material is dried to carry the odor eliminating compositions to the sheet-shaped supporting material. In this method, the odor eliminating compositions are given by the coating method, the productivity can be improved remarkably and the carried amount can be controlled with high accuracy. The technique of the coating is not limited to a specific one, and the examples include, for example, a gravure roll process, a spray process, a roll coater, a jet print process, transfer print process and a screen print process.

The drying method is not limited to a specific one. Air drying or heat treatment can be employed. In view of the efficiency of drying, it is preferable to employ a heat treatment.

The processing technique is not limited to the aforementioned example. For example, the odor eliminating compositions can be applied to the fibers constituting the nonwoven fabric sheet in advance.

The application of the odor eliminating material 1 according to the third aspect of the present invention is not limited to a specific one. For example, an odor eliminating sheet for building materials, an odor eliminating filter for air-conditioning systems such as air conditioners and an odor eliminating filter for various odors eliminating apparatuses can be exemplified.

Next, concrete examples according to the first and second aspect of the present invention will be explained.

EXAMPLE 1

A cotton nonwoven fabric (weight per unit area: 100 g/m²) was immersed in an aqueous solution of 3-chloro-2-hydroxypropyl trimethyl ammoniumchloride (quaternary ammonium salt) (concentration: 7.5 mass %) for 5 (five) minutes to perform a cationization treatment of the cotton nonwoven fabric. Subsequently, this nonwoven fabric was immersed in an aqueous solution (concentration: 0.5 mass %) of diethylhexylnatrium sulfosuccinate (alkylsuccinic acid) for 5 (five) minutes. Then, the nonwoven fabric taken out of the solution was further immersed in an aqueous solution (concentration: 0.5 mass %) of cobalt phthalocyanine polysulfonic acid natrium (cobalt phthalocyanine complex) for 5 (five) minutes. Thereafter, the nonwoven fabric taken out of the solution was wrung with a mangle to obtain an odor eliminating sheet. The chemical formula of the diethylhexylnatrium sulfosuccinate is shown in the following chemical formula (II).

[FORMULA 3]

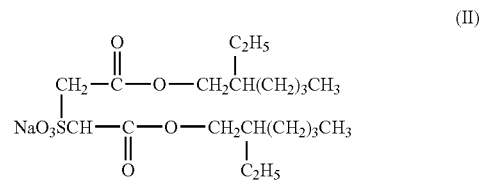

EXAMPLE 2

An odor eliminating sheet was obtained in the same manner as in Example 1, except that sodium lauryl sulfonate (alkyl sulfonic acid) solution (concentration: 0.5 mass %) was used in place of diethylhexylnatrium sulfosuccinate.

EXAMPLE 3

A cotton nonwoven fabric (weight per unit area: 100 g/m²) was immersed in an aqueous solution of 3-chloro-2-hydroxypropyl trimethylammoniumchloride (quaternary ammonium salt) (concentration: 7.5 mass %) for 5 (five) minutes to perform a cationization treatment of the cotton nonwoven fabric. Subsequently, this nonwoven fabric was immersed in an aqueous solution of cobalt phthalocyanine polysulfonic acid natrium (cobalt phthalocyanine complex) and polyacrylamide (migration inhibitor) (concentration: 0.5 mass % respectively) for 5 (five) minutes. Thereafter, the nonwoven fabric taken out of the solution was wrung with a mangle to obtain an odor eliminating sheet.

EXAMPLE 4

An odor eliminating sheet was obtained in the same manner as in Example 1, except that a paper-sheet (weight per unit area: 100 g/m$^2$) made of cellulose (pulp) was used in place of the cotton nonwoven fabric.

EXAMPLE 5

An odor eliminating sheet was obtained in the same manner as in Example 1, except that a rayon woven fabric (weight per unit area: 100 g/m$^2$) was used in place of the cotton nonwoven fabric.

EXAMPLE 6

An odor eliminating sheet was obtained in the same manner as in Example 1, except that a wool knitted fabric (weight per unit area: 100 g/m$^2$) was used in place of the cotton nonwoven fabric.

EXAMPLE 7

An odor eliminating sheet was obtained in the same manner as in Example 1, except that a porous three dimension structure (43 mm in length×55 mm in width×12 mm in thickness) in which flat sheets 3 and wavy sheets 4 made of bleached kraft paper were integrally laminated alternatively, as shown in FIGS. 1 and 2, was used in place of the cotton nonwoven fabric as the supporting material.

EXAMPLE 8

An odor eliminating sheet was obtained in the same manner as in Example 2, except that a porous three dimension structure (43 mm in length×55 mm in width×12 mm in thickness) in which flat sheets 3 and wavy sheets 4 made of bleached kraft paper were integrally laminated alternatively, as shown in FIGS. 1 and 2, was used in place of the cotton nonwoven fabric as the supporting material.

EXAMPLE 9

An odor eliminating sheet was obtained in the same manner as in Example 3, except that a porous three dimension structure (43 mm in length×55 mm in width×12 mm in thickness) in which flat sheets 3 and wavy sheets 4 made of bleached kraft paper were integrally laminated alternatively, as shown in FIGS. 1 and 2, was used in place of the cotton nonwoven fabric as the supporting material.

COMPARATIVE EXAMPLE 1

A cotton nonwoven fabric (weight per unit area: 100 g/m$^2$) was immersed in an aqueous solution (concentration: 0.5 mass %) of cobalt phthalocyanine polysulfonic acid natrium (cobalt phthalocyanine complex) for 5 (five) minutes. Thereafter, the nonwoven fabric taken out of the solution was wrung with a mangle to obtain an odor eliminating sheet.

COMPARATIVE EXAMPLE 2

A cotton nonwoven fabric (weight per unit area: 100 g/m$^2$) was immersed in an aqueous solution of 3-chloro-2-hydroxypropyl trimethylammoniumchloride (quaternary ammonium salt) (concentration: 7.5 mass %) for 5 (five) minutes to perform a cationization treatment of the cotton nonwoven fabric. Subsequently, this nonwoven fabric was immersed in an aqueous solution (concentration: 0.5 mass %) of cobalt phthalocyanine polysulfonic acid natrium (cobalt phthalocyanine complex) for 5 (five) minutes. Thereafter, the nonwoven fabric taken out of the solution was wrung with a mangle and dried to obtain an odor eliminating sheet.

EXAMPLE 10

An odor eliminating sheet was obtained in the same manner as in Example 1, except that an aqueous solution (concentration: 0.5 mass %) of polyoxyethylene (3) sodium lauryl sulfonate (polyalkylether sufonic acid) was used in place of the diethylhexylnatrium sulfosuccinate. The chemical formula of polyoxyethylene (3) sodium lauryl sulfonate is $C_{12}H_{25}O(CH_2CH_2O)_3SO_3Na$.

EXAMPLE 11

An odor eliminating sheet was obtained in the same manner as in Example 1, except that an aqueous solution (concentration: 0.5 mass %) of polyoxyethylene (12) cetylether (polyoxyethylene alkylether) was used in place of the diethylhexylnatrium sulfosuccinate. The chemical formula of polyoxyethylene (12) cetylether is $C_{16}H_{33}O(CH_2CH_2O)_{12}H$.

EXAMPLE 12

An odor eliminating sheet was obtained in the same manner as in Example 3, except that sodium alginate was used in place of polyacrylamide.

The carried amount of metal phthalocyanine complex in each odor eliminating material manufactured as mentioned above was measured by ICP optical emission spectrometry (quantitative determination of cobalt atom). The results are shown in Table 1. As will be apparent from Table 1, in the odor eliminating materials according to Examples 1 to 12, the carried amount of metal phthalocyanine complex is increased remarkably as compared with the odor eliminating materials of Comparative examples 1 and 2.

TABLE 1

| | CARRIED AMOUNT OF METAL PHTHALOCYANINE COMPLEX (ppm) |
|---|---|
| Example 1 | 6451 |
| Example 2 | 6217 |
| Example 3 | 19649 |
| Example 4 | 5531 |
| Example 5 | 5790 |
| Example 6 | 6605 |
| Example 7 | 5296 |
| Example 8 | 4827 |
| Example 9 | 13711 |
| Comparative Example 1 | 1173 |
| Comparative Example 2 | 1650 |
| Example 10 | 5498 |
| Example 11 | 5703 |
| Example 12 | 15625 |

The evaluation of odor elimination performance of each odor eliminating material was performed in accordance with the following test methods.

<Odor Elimination Test Method>

(Ammonia Odor Elimination Performance)

A test piece (10×10 cm: square) cut out from each odor eliminating material was put in a bag of 2 L capacity, and then ammonia gas was injected in the bag so that the concentration becomes 100 ppm. After 60 minutes have passed since the ammonia gas was injected, the residual concentration of the ammonia gas was measured. Then, the total amount of ammonia gas captured by each test piece was calculated based on the measured value, and then the elimination rate (%) of ammonia gas was calculated.

(Hydrogen Sulfide Odor Elimination Performance)

The elimination rate (%) of hydrogen sulfide was calculated in the same manner as in the above test, except that hydrogen sulfide gas was injected in place of ammonia gas so that the concentration thereof in the bag becomes 10 ppm.

(Methyl Mercaptan Odor Elimination Performance)

The elimination rate (%) of methyl mercaptan was calculated in the same manner as in the above test, except that methyl mercaptan gas was injected in place of ammonia gas so that the concentration thereof in the bag becomes 10 ppm.

(Acetic Acid Odor Elimination Performance)

The elimination rate (%) of acetic acid was calculated in the same manner as in the above test, except that acetic acid gas was injected in place of ammonia gas so that the concentration thereof in the bag becomes 10 ppm.

(Acetaldehyde Odor Elimination Performance)

The elimination rate (%) of acetaldehyde was calculated in the same manner as in the above test, except that acetaldehyde gas was injected in place of ammonia gas so that the concentration thereof in the bag becomes 10 ppm.

In the evaluation, "⊚" denotes that the elimination rate is 95% or more, "○" denotes that the elimination rate is not less than 90% but less than 95%, "Δ" denotes that the elimination rate is not less than 85% but less than 90%, and "X" denotes that the elimination rate is less than 85%.

As will be apparent from Table 2, the odor eliminating materials of Examples 1 to 12 exerted excellent odor elimination performance against ammonia, hydrogen sulfide, methyl mercaptan, acetic acid and acetaldehyde.

To the contrary, in the odor eliminating material of Comparative example 1 in which metal phthalocyanine complex was simply carried and the odor eliminating material of Comparative example 2 in which metal phthalocyanine complex was carried after the cationization treatment, enough odor eliminating performance could not be obtained.

Next, concrete examples according to the third aspect of the present invention will be explained.

EXAMPLE 13

Sebacic acid dihydrazide of 0.45 weight parts and cobalt phthalocyanine complex (cobalt phthalocyanine polysulfonic natrium) of 0.05 weight parts were added to water of 79.5 weight parts, and then agitated with an agitator to thereby obtain dispersion liquid. Then, acrylate resin (solid content: 50%) of 20 weight parts is added to the dispersion liquid and agitated well to obtain even dispersion liquid (treatment solution). A spunbonded nonwoven fabric (weight per unit area: 40 g/m$^2$) was immersed in the treatment solution, and then taken out of the solution and wrung with a mangle and dried to obtain an odor eliminating sheet.

EXAMPLES 14 TO 19, COMPARATIVE EXAMPLES 3 AND 4

An odor eliminating sheet was obtained in the same manner as in Example 13, except that the test was performed by using the treatment agent shown in Table 3 under the condition shown in Table 3.

TABLE 2

ODOR ELIMINATION PERFORMANCE TEST

| | AMMONIA | | HYDROGEN SULFIDE | | METHYL-MERCAPTAN | | ACETIC ACID | | ACETALDEHYDE | |
| --- | --- | --- | --- | --- | --- | --- | --- | --- | --- | --- |
| | ELIMINATION RATE (%) | EVALUATION | ELIMINATION RATE (%) | EVALUATION | ELIMINATION RATE (%) | EVALUATION | ELIMINATION RATE (%) | EVALUATION | ELIMINATION RATE (%) | EVALUATION |
| Ex. 1 | 96 | ⊚ | 95 | ⊚ | 92 | ○ | 90 | ○ | 91 | ○ |
| Ex. 2 | 96 | ⊚ | 93 | ○ | 92 | ○ | 90 | ○ | 90 | ○ |
| Ex. 3 | 100 | ⊚ | 100 | ⊚ | 98 | ⊚ | 96 | ⊚ | 96 | ⊚ |
| Ex. 4 | 98 | ⊚ | 97 | ⊚ | 92 | ○ | 87 | Δ | 91 | ○ |
| Ex. 5 | 96 | ⊚ | 97 | ⊚ | 92 | ○ | 90 | ○ | 92 | ○ |
| Ex. 6 | 100 | ⊚ | 100 | ⊚ | 95 | ⊚ | 94 | ○ | 90 | ○ |
| Ex. 7 | 93 | ○ | 95 | ⊚ | 90 | ○ | 88 | Δ | 85 | Δ |
| Ex. 8 | 91 | ○ | 93 | ○ | 89 | Δ | 85 | Δ | 86 | Δ |
| Ex. 9 | 100 | ⊚ | 100 | ⊚ | 97 | ⊚ | 95 | ⊚ | 96 | ⊚ |
| Com. Ex. 1 | 71 | X | 74 | X | 62 | X | 42 | X | 47 | X |
| Com. Ex. 2 | 86 | Δ | 91 | ○ | 78 | X | 58 | X | 63 | X |
| Ex. 10 | 96 | ⊚ | 95 | ⊚ | 92 | ○ | 91 | ○ | 90 | ○ |
| Ex. 11 | 95 | ⊚ | 95 | ⊚ | 90 | ○ | 90 | ○ | 92 | ○ |
| Ex. 12 | 100 | ⊚ | 100 | ⊚ | 96 | ⊚ | 95 | ⊚ | 96 | ⊚ |

TABLE 3

|  |  |  | Example | | | | | | | Com. Example | |
|---|---|---|---|---|---|---|---|---|---|---|---|
|  |  |  | 13 | 14 | 15 | 16 | 17 | 18 | 19 | 3 | 4 |
| Composition/ weight parts | Odor eliminating compositions | Sebacic acid dihidrazide | 0.45 | 0.45 | — | 0.42 | 0.40 | 0.48 | 0.35 | — | 0.50 |
|  |  | Dodecanedioic acid dihydrazide | — | — | 0.45 | — | — | — | — | — | — |
|  |  | Cobalt phthalocyanine complex | 0.05 | 0.05 | 0.05 | 0.08 | 0.10 | 0.02 | 0.15 | 0.50 | — |
|  |  | zeolite | — | 2 | 2 | 2 | 2 | 2 | 2 | 2 | 2 |
|  |  | acrylate resin | 20 | 20 | 20 | 20 | 20 | 20 | 20 | 20 | 20 |
|  | water |  | 79.5 | 77.5 | 77.5 | 77.5 | 77.5 | 77.5 | 77.5 | 77.5 | 77.5 |
| Carried amount of odor eliminating compositions with respect to supporting material (wt %) | | | 0.9 | 1.8 | 1.8 | 1.7 | 1.7 | 1.8 | 1.6 | 1.3 | 2.2 |
| Supporting material | | | Sheet A | Sheet A | Sheet A | Sheet A | Sheet A | Sheet A | Sheet A | Sheet A | Sheet A |
| Manufacturing method | | | Immersion | Immersion | Immersion | Immersion | Immersion | Immersion | Immersion | Immersion | Immersion |

*Sheet A: Spunbonded nonwoven fabric made of polyester (weight per unit area: 40 g/m$^2$)

EXAMPLE 20

An odor eliminating sheet was obtained in the same manner as in Example 14, except that a porous structure (43 mm in length×55 mm in width×12 mm in thickness) in which flat sheets 3 and wavy sheets 4 made of bleached kraft paper were integrally laminated alternatively, as shown in FIGS. 1 and 2, was used in place of the spunbonded nonwoven fabric as the supporting material.

EXAMPLE 21

An odor eliminating sheet was obtained in the same manner as in Example 15, except that a porous structure (43 mm in length×55 mm in width×12 mm in thickness) in which flat sheets 3 and wavy sheets 4 made of bleached kraft paper were integrally laminated alternatively, as shown in FIGS. 1 and 2, was used in place of the spunbonded nonwoven fabric as the supporting material.

EXAMPLE 22

Sebacic acid dihydrazide of 0.45 weight parts and cobalt phthalocyanine complex (cobalt phthalocyanine polysulfonic natrium) of 0.05 weight parts were added to water of 79.5 weight parts, and then agitated with an agitator to thereby obtain dispersion liquid. Then, acrylate resin (solid content: 50%) of 20 weight parts is added to the dispersion liquid and agitated well to obtain even dispersion liquid (treatment solution). This treatment liquid was dot-printed to a polypropylene nonwoven fabric (made by a melt blow method) whose weight per unit area is 70 g/m$^2$ by using a gravure roll applicator, and then dried to thereby obtain an odor eliminating sheet.

EXAMPLE 23

An odor eliminating sheet was obtained in the same manner as in Example 22, except that the test was performed by using the treatment agent shown in Table 4 under the condition shown in Table 4.

TABLE 4

|  |  |  | Example | | | |
|---|---|---|---|---|---|---|
|  |  |  | 20 | 21 | 22 | 23 |
| Composition/ weight parts | Odor eliminating compositions | Sebacic acid dihidrazide | 0.45 | — | 0.45 | — |
|  |  | Dodecanedioic acid dihydrazide | — | 0.45 | — | 0.45 |
|  |  | Cobalt phthalocyanine complex | 0.05 | 0.05 | 0.05 | 0.05 |
|  |  | zeolite | 2 | 2 | 2 | 2 |
|  |  | acrylate resin | 20 | 20 | 20 | 20 |
|  | water |  | 77.5 | 77.5 | 77.5 | 77.5 |
| Carried amount of odor eliminating compositions with respect to supporting material (wt %) | | | 3.5 | 3.5 | 1.8 | 1.8 |

TABLE 4-continued

|  | Example | | | |
|---|---|---|---|---|
|  | 20 | 21 | 22 | 23 |
| Supporting material | Porous | Porous | Sheet B | Sheet B |
| Manufacturing method | Immersion | Immersion | Print | Print |

*Sheet B: Polypropylene nonwoven fabric manufactured by a melt blow method (weight per unit area: 70 g/m$^2$)
*Porous: Integrally laminated flat and wavy sheets made of bleached kraft paper The evaluation of odor elimination performance of each odor eliminating material was performed in accordance with the following test methods. The results are shown in Tables 5 and 6.

<Odor Elimination Performance Test Method a (Performance Evaluation as Odor Eliminating Sheet)>

(Ammonia Odor Elimination Performance)

A test piece (10×10 cm: square) cut out from each odor eliminating material was put in a bag of 2 L capacity, and then ammonia gas was injected in the bag so that the concentration becomes 100 ppm. After 10 minutes have passed since the ammonia gas was injected, the residual concentration of the ammonia gas was measured. Then, the total amount of ammonia gas captured by each test piece was calculated based on the measured value, and then the elimination rate (%) of ammonia gas was calculated.

(Hydrogen Sulfide Odor Elimination Performance)

The elimination rate (%) of hydrogen sulfide was calculated in the same manner as in the above test, except that hydrogen sulfide gas was injected in place of ammonia gas so that the concentration thereof in the bag becomes 10 ppm.

(Methyl Mercaptan Odor Elimination Performance)

The elimination rate (%) of methyl mercaptan was calculated in the same manner as in the above test, except that methyl mercaptan gas was injected in place of ammonia gas so that the concentration thereof in the bag becomes 10 ppm.

(Acetic Acid Odor Elimination Performance)

The elimination rate (%) of acetic acid was calculated in the same manner as in the above test, except that acetic acid gas was injected in place of ammonia gas so that the concentration thereof in the bag becomes 10 ppm.

(Acetaldehyde Odor Elimination Performance)

The elimination rate (%) of acetaldehyde was calculated in the same manner as in the above test, except that acetaldehyde gas was injected in place of ammonia gas so that the concentration thereof in the bag becomes 10 ppm.

In the evaluation, "⊙" denotes that the elimination rate is 95% or more, "○" denotes that the elimination rate is not less than 90% but less than 95%, "Δ" denotes that the elimination rate is not less than 85% but less than 90%, and "X" denotes that the elimination rate is less than 85%.

TABLE 5

| | ODOR ELIMINATION PERFORMANCE TEST A | | | | | | | | | |
|---|---|---|---|---|---|---|---|---|---|---|
| | AMMONIA | | HYDROGEN SULFIDE | | METHYL-MERCAPTAN | | ACETIC ACID | | ACETALDEHYDE | |
| | ELIMI-NATION RATE (%) | EVALU-ATION | ELIMI-NATION RATE (%) | EVALU-ATION | ELIMINATION RATE (%) | EVALU-ATION | ELIMINATION RATE (%) | EVALU-ATION | ELIMINATION RATE (%) | EVALU-ATION |
| Ex. 13 | 95.3 | ⊙ | 95.0 | ⊙ | 92.9 | ○ | 91.7 | ○ | 95.0 | ⊙ |
| Ex. 14 | 98.1 | ⊙ | 99.3 | ⊙ | 96.7 | ⊙ | 98.0 | ⊙ | 95.8 | ⊙ |
| Ex. 15 | 98.8 | ⊙ | 99.5 | ⊙ | 97.3 | ⊙ | 98.5 | ⊙ | 97.3 | ⊙ |
| Ex. 16 | 95.6 | ⊙ | 98.9 | ⊙ | 96.3 | ⊙ | 98.0 | ⊙ | 95.4 | ⊙ |
| Ex. 17 | 95.2 | ⊙ | 96.4 | ⊙ | 95.1 | ⊙ | 95.4 | ⊙ | 95.1 | ⊙ |
| Ex. 18 | 92.7 | ○ | 94.8 | ○ | 88.5 | Δ | 89.3 | Δ | 93.4 | ○ |
| Ex. 19 | 86.4 | Δ | 93.7 | ○ | 91.1 | ○ | 92.0 | ○ | 88.6 | Δ |
| Com. Ex. 3 | 42.9 | X | 71.1 | X | 85.3 | Δ | 88.8 | Δ | 40.3 | X |
| Com. Ex. 4 | 88.1 | Δ | 85.9 | Δ | 33.8 | X | 47.0 | X | 87.0 | Δ |
| Ex. 20 | 99.2 | ⊙ | 99.5 | ⊙ | 97.8 | ⊙ | 99.2 | ⊙ | 96.8 | ⊙ |
| Ex. 21 | 99.2 | ⊙ | 100.0 | ⊙ | 98.3 | ⊙ | 99.2 | ⊙ | 96.0 | ⊙ |
| Ex. 22 | 97.6 | ⊙ | 96.6 | ⊙ | 95.3 | ⊙ | 95.1 | ⊙ | 95.5 | ⊙ |
| Ex. 23 | 97.6 | ⊙ | 97.8 | ⊙ | 96.0 | ⊙ | 95.1 | ⊙ | 95.5 | ⊙ |

<Odor Elimination Performance Test Method B (Performance Evaluation as Odor Eliminating Filter)>

A circular test piece (Diameter: 50 mm) cut out from each odor eliminating sheet was fixed to a sample holder disposed at a longitudinal middle portion in an elongated cylindrical tube, and fart was introduced into the cylindrical tube from one end thereof at the rate of 5 L/minute. The gas concentration before passing through the sample holder and the gas concentration after passing through the sample holder were measured by a detecting tube. Based on these measured values, the total amount of each fart captured by each test piece was calculated, and then the elimination rate (%) of the fart was obtained.

In the evaluation, "⊚" denotes that the elimination rate is 70% or more, "○" denotes that the elimination rate is not less than 50% but less than 70%, "Δ" denotes that the elimination rate is not less than 45% but less than 50%, and "X" denotes that the elimination rate is less than 45%.

The gas concentration before passing through the sample holder was set to be 100 ppm in the case of ammonia gas and 10 ppm in the case of hydrogen sulfide, methyl mercaptan, acetic acid and acetaldehyde respectively.

TABLE 6

ODOR ELIMINATION PERFORMANCE TEST B

| | AMMONIA | | HYDROGEN SULFIDE | | METHYL-MERCAPTAN | | ACETIC ACID | | ACETALDEHYDE | |
|---|---|---|---|---|---|---|---|---|---|---|
| | ELIMINATION RATE (%) | EVALUATION | ELIMINATION RATE (%) | EVALUATION | ELIMINATION RATE (%) | EVALUATION | ELIMINATION RATE (%) | EVALUATION | ELIMINATION RATE (%) | EVALUATION |
| Ex. 13 | 58.7 | ○ | 52.1 | ○ | 54.3 | ○ | 50.9 | ○ | 55.7 | ○ |
| Ex. 14 | 80.3 | ⊚ | 78.2 | ⊚ | 72.5 | ⊚ | 73.0 | ⊚ | 76.9 | ⊚ |
| Ex. 15 | 80.6 | ⊚ | 80.5 | ⊚ | 73.4 | ⊚ | 75.8 | ⊚ | 76.9 | ⊚ |
| Ex. 16 | 78.4 | ⊚ | 75.4 | ⊚ | 71.3 | ⊚ | 72.2 | ⊚ | 73.0 | ⊚ |
| Ex. 17 | 71.1 | ⊚ | 70.8 | ⊚ | 70.5 | ⊚ | 70.5 | ⊚ | 70.8 | ⊚ |
| Ex. 18 | 48.3 | Δ | 45.9 | Δ | 49.2 | Δ | 47.6 | Δ | 53.6 | ○ |
| Ex. 19 | 49.6 | Δ | 67.6 | ○ | 68.4 | ○ | 65.8 | ○ | 48.4 | Δ |
| Com. Ex. 3 | 43.0 | X | 40.7 | X | 46.2 | Δ | 45.8 | Δ | 40.8 | X |
| Com. Ex. 4 | 45.3 | Δ | 47.1 | Δ | 34.0 | X | 41.3 | X | 45.5 | Δ |
| Ex. 22 | 75.1 | ⊚ | 68.2 | ○ | 60.2 | ○ | 62.1 | ○ | 67.2 | ○ |
| Ex. 23 | 76.9 | ⊚ | 65.9 | ○ | 63.4 | ○ | 60.8 | ○ | 67.8 | ○ |

As will be apparent from Tables 5 and 6, the odor eliminating materials of Examples 13 to 23 exerted excellent odor elimination performance against any of ammonia, hydrogen sulfide, methyl mercaptan, acetic acid and acetaldehyde. Especially, in Examples 13 to 17 and 20 to 23 in which the weight ratio of hydrazine derivative/metal phthalocyanine complex falls within a range of 75/25 to 95/5, the odor elimination performance was excellent.

To the contrary, in Comparative Example 3 in which only metal phthalocyanine complex was carried and in Comparative Example 4 in which only the hydrazine derivative was carried, sufficient odor elimination performance could not be obtained.

While illustrative embodiments of the present invention have been described herein, the present invention is not limited to the various preferred embodiments described herein, but includes any and all embodiments having modifications, omissions, combinations (e.g., of aspects across various embodiments), adaptations and/or alterations as would be appreciated by those in the art based on the present disclosure. The limitations in the claims are to be interpreted broadly based the language employed in the claims and not limited to examples described in the present specification or during the prosecution of the application, which examples are to be construed as non-exclusive. For example, in the present disclosure, the term "preferably" is non-exclusive and means "preferably, but not limited to." Means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited.

What is claimed is:

1. An odor eliminating material, comprising:
a cationized supporting material; and
a metal phthalocyanine complex carried by the supporting material,
wherein the supporting material is treated by a treatment agent containing a metal phthalocyanine complex and a level dyeing agent, or treated by a treatment agent containing a level dyeing agent and then further treated by a treatment agent containing a metal phthalocyanine complex, whereby the metal phthalocyanine complex is carried by the supporting material.

2. An odor eliminating material, comprising:
a cationized supporting material;
a metal phthalocyanine complex carried by the supporting material; and
a level dyeing agent carried by the supporting material.

3. The odor eliminating material as recited in claim 1 or 2, wherein the level dyeing agent is one or more compounds selected from the group consisting of polyalkylether sulfonic acid, polyoxyethylene alkylether, alkyl succinic acid and alkyl sulfonic acid.

4. An odor eliminating material, comprising:
a cationized supporting material; and
a metal phthalocyanine complex carried by the supporting material,
wherein the supporting material is treated by a treatment agent containing a metal phthalocyanine complex and a migration inhibitor, or treated by a treatment agent containing a migration inhibitor and then further treated by a treatment agent containing a metal phthalocyanine complex, whereby the metal phthalocyanine complex is carried by the supporting material.

5. An odor eliminating material, comprising:
a cationized supporting material;
a metal phthalocyanine complex carried by the supporting material; and
a migration inhibitor carried by the supporting material.

6. The odor eliminating material as recited in claim 4 or 5, wherein the migration inhibitor is one or more compounds selected from the group consisting of acrylamide series polymer and sodium alginate.

7. The odor eliminating material as recited in any one of claims 1, 2, 4 and 5, wherein a constituent material of the supporting material is one or more materials selected from the group consisting of cellulose, rayon, cotton and wool.

8. The odor eliminating material as recited in any one of claims 1, 2, 4 and 5, wherein the supporting material is constituted by a sheet made of any one of nonwoven fabric, woven fabric, knitted fabric and paper.

9. The odor eliminating material as recited in any one of claims 1, 2, 4 and 5, wherein the supporting material is a material cationized by quaternary ammonium salt.

10. The odor eliminating material as recited in any one of claims 1, 2, 4 and 5, wherein a carried amount of the metal phthalocyanine complex is 3,000 ppm or more with respect to the supporting material.

11. The odor eliminating material as recited in any one of claims 1, 2, 4 and 5, wherein the metal phthalocyanine complex is a cobalt phthalocyanine complex.

12. The odor eliminating material as recited in any one of claims 1, 2, 4 and 5, wherein the supporting material further carries a hydrazine derivative.

13. A method for manufacturing an odor eliminating material, the method comprising:
cationizing a supporting material;
immersing the cationized supporting material into a treatment solution containing a level dyeing agent; and
immersing the supporting material treated in the treatment solution into a treatment solution containing a metal phthalocyanine complex and then drying the supporting material.

14. The method for manufacturing an odor eliminating material as recited in claim 13, wherein one or more compounds selected from the group consisting of polyalkylether sulfonic acid, polyoxyethylene alkylether, alkyl succinic acid and alkyl sulfonic acid is used as the level dyeing agent.

15. A method for manufacturing an odor eliminating material, the method comprising:
cationizing a supporting material; and
immersing the cationized supporting material into a treatment solution containing a metal phthalocyanine complex and a migration inhibitor and then drying the supporting material.

16. The method for manufacturing an odor eliminating material as recited in claim 15, wherein one or more compounds selected from the group consisting of acrylamide series polymer and sodium alginate is used as the migration inhibitor.

17. The method for manufacturing an odor eliminating material as recited in claim 15, wherein a mass ratio of the metal phthalocyanine complex/the migration inhibitor in the treatment solution falls within a range of 1/10 to 10/1.

18. The method for manufacturing an odor eliminating material as recited in claim 15, wherein a mass ratio of the metal phthalocyanine complex/the migration inhibitor in the treatment solution falls within a range of 1/2 to 5/1.

19. An odor eliminating material, comprising:
a supporting material; and
an odor eliminating compound carried by the supporting material,
wherein the supporting material is treated by a treatment agent containing the odor eliminating compound including a hydrazine derivative and a metal phthalocyanine complex, whereby the odor eliminating compound is carried by the supporting material.

20. The odor eliminating material as recited in claim 19, wherein a weight ratio of the hydrazine derivative and the metal phthalocyanine complex in the treatment agent falls within a range of 75/25 to 95/5.

21. The odor eliminating material as recited in claim 19, wherein the odor eliminating compound further contains a porous inorganic substance.

22. The odor eliminating material as recited in claim 21, wherein the porous inorganic substance is zeolite.

23. The odor eliminating material as recited in claim 19, wherein the odor eliminating compound further contains binder resin.

24. The odor eliminating material as recited in claim 19, wherein the metal phthalocyanine complex is cobalt phthalocyanine complex.

25. The odor eliminating material as recited in claim 19, wherein a carried amount of the odor eliminating compound falls within a range of 0.1 to 10 wt % with respect to the supporting material.

26. The odor eliminating material as recited in claim 19, wherein the supporting material is a nonwoven fabric.

27. The odor eliminating material as recited in claim 19, wherein the supporting material is porous structure material.

28. The odor eliminating material as recited in claim 19, wherein the hydrazine derivative is a reaction product of one or two compounds selected from the group consisting of hydrazine and semicarbazide and one or more compounds selected from the group consisting of monocarboxylic acid having the carbon number of 8 to 16, dicarboxylic acid, aromatic monocarboxylic acid and aromatic dicarboxylic acid.

29. The odor eliminating material as recited in claim 19, wherein the hydrazine derivative is a reaction product of one or two compounds selected from the group consisting of hydrazine and semicarbazide and one or more compounds selected from the group consisting of monoglycidyl derivative and diglycidyl derivative whose carbon number is 8 to 16.

30. The odor eliminating material as recited in claim 19, wherein the hydrazine derivative is one or more compounds selected from the group consisting of sebacic acid dihydrazide, dodecane diacid dihydrazide and isophthalic acid dihydrazide.

31. A method for manufacturing an odor eliminating material, comprising:
immersing a supporting material into a treatment agent containing an odor eliminating composite including a hydrazine derivative and a metal phthalocyanine complex; and
drying the supporting material to thereby carry the odor eliminating composite.

32. A method for manufacturing an odor eliminating material, comprising:
coating a treatment agent containing an odor eliminating composite including a hydrazine derivative and a metal phthalocyanine complex on a sheet-like supporting material; and
drying the supporting material to thereby carry the odor eliminating composite.

33. The method for manufacturing an odor eliminating material as recited in claim 31 or 32, wherein a weight ratio of the hydrazine derivative/the metal phthalocyanine complex falls within a range of 75/25 to 95/5.

* * * * *